United States Patent [19]
Horton

[11] Patent Number: 6,090,125
[45] Date of Patent: *Jul. 18, 2000

[54] ANATOMICALLY SHAPED VASOOCCLUSIVE DEVICE AND METHOD OF MAKING THE SAME

[75] Inventor: Joseph A. Horton, Charleston, S.C.

[73] Assignee: MUSC Foundation for Research Development, Charleston, S.C.

[*] Notice: This patent issued on a continued prosecution application filed under 37 CFR 1.53(d), and is subject to the twenty year patent term provisions of 35 U.S.C. 154(a)(2).

[21] Appl. No.: 09/089,328

[22] Filed: Jun. 2, 1998

Related U.S. Application Data

[63] Continuation of application No. 08/799,439, Feb. 13, 1997, Pat. No. 5,766,219, which is a continuation of application No. 08/425,106, Apr. 20, 1995, Pat. No. 5,645,558.

[51] Int. Cl.⁷ .................................................. A61M 29/00
[52] U.S. Cl. .......................... 606/191; 606/158; 606/198
[58] Field of Search .................................. 606/191, 198, 606/200, 151, 152, 158

[56] References Cited

U.S. PATENT DOCUMENTS

| | | |
|---|---|---|
| 1,341,052 | 5/1920 | Gale . |
| 1,667,730 | 5/1928 | Birchard Green . |
| 2,078,182 | 4/1937 | MacFarland . |
| 2,549,335 | 4/1951 | Rahthus . |
| 3,334,629 | 8/1967 | Cohn . |
| 3,649,224 | 3/1972 | Anderson et al. . |
| 3,868,956 | 3/1975 | Alfidi et al. . |
| 4,097,336 | 3/1990 | Gianturco . |

(List continued on next page.)

FOREIGN PATENT DOCUMENTS

| | | |
|---|---|---|
| 0 183372 | 6/1986 | European Pat. Off. . |
| 0 382014 A1 | 8/1990 | European Pat. Off. . |
| 0518704A1 | 12/1992 | European Pat. Off. . |
| 592182 | 7/1925 | France . |
| 3203410 A1 | 11/1982 | Germany . |
| 4102550 A1 | 8/1991 | Germany . |
| 2 066 839 | 7/1981 | United Kingdom . |
| WO92/14408 | 9/1992 | WIPO . |
| WO 94/09705 | 5/1994 | WIPO . |
| WO 94/10936 | 5/1994 | WIPO . |
| WO94/16629 | 8/1994 | WIPO . |
| WO97/31672 | 9/1997 | WIPO . |

OTHER PUBLICATIONS

Christos A. Athanasoulis, M.D. The New England Journal of Medicine, May 15, 1980 "Therapeutic Applications of Angiography" pp. 1117–1125 (1 of 2).

Christos A. Athanasoulis, M.D. The New England Journal of Medicine, May 22, 1980 "Therapeutic Applications of Angiography" pp. 1174–1179 (2 of 2).

Alex Berenstein, M.D. and Irvin I. Kricheff, M.D. "Catheter and Material Selection for Transarterial Embolization: Technical Considerations" Radiology, Sep. 1979; pp. 631–639.

(List continued on next page.)

*Primary Examiner*—Michael Buiz
*Assistant Examiner*—Daphna Shai
*Attorney, Agent, or Firm*—Fulwider Patton Lee & Utecht, LLP

[57] ABSTRACT

This invention is an occlusive device for inserting into body cavities or vesicles. More particularly, it is a vasoocclusive device which, as used, is in the approximate shape of an anatomical cavity. It may be ultimately deployed as a substantially spherical shape in the operable configuration. The device is a self-forming shape made from a pre-formed occlusive strand of flexible material. The occlusive strand may be helically coiled or braided and may be adapted with various polymeric fibers. The device is typically introduced through a catheter in the substantially linear inoperable configuration. The invention provides a plurality of such substantially spherical strand portions which nest concentrically with each other in the operable configuration. The invention also includes methods of producing and using the substantially spherical occlusive devices.

3 Claims, 4 Drawing Sheets

U.S. PATENT DOCUMENTS

| | | |
|---|---|---|
| 4,205,680 | 6/1980 | Marshall . |
| 4,494,531 | 1/1985 | Gianturco . |
| 4,512,338 | 4/1985 | Balko et al. . |
| 4,553,545 | 11/1985 | Maass et al. . |
| 4,638,803 | 1/1987 | Rand . |
| 4,655,771 | 4/1987 | Wallsten . |
| 4,718,907 | 1/1988 | Karwoski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,922,924 | 5/1990 | Gambale et al. . |
| 4,954,126 | 9/1990 | Wallsten . |
| 4,957,479 | 9/1990 | Roemer . |
| 4,957,501 | 9/1990 | Lahille et al. . |
| 4,990,155 | 2/1991 | Wilkoff . |
| 4,994,069 | 2/1991 | Richart et al. .......................... 606/191 |
| 5,015,253 | 5/1991 | MacGregor . |
| 5,019,090 | 5/1991 | Pinchuk . |
| 5,025,799 | 6/1991 | Wilson . |
| 5,026,377 | 6/1991 | Burton et al. . |
| 5,041,084 | 8/1991 | DeVries et al. . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,122,136 | 6/1992 | Guglielmi et al. . |
| 5,133,731 | 7/1992 | Butler et al. . |
| 5,133,732 | 7/1992 | Wiktor . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,221,269 | 6/1993 | Miller et al. . |
| 5,222,969 | 6/1993 | Gillis . |
| 5,226,911 | 7/1993 | Chee et al. . |
| 5,228,453 | 7/1993 | Sepetka . |
| 5,234,456 | 8/1993 | Silvestrini . |
| 5,238,004 | 8/1993 | Sahatjian et al. . |
| 5,250,071 | 10/1993 | Palermo . |
| 5,251,640 | 10/1993 | Osborne . |
| 5,256,146 | 10/1993 | Ensminger et al. . |
| 5,304,194 | 4/1994 | Chee et al. . |
| 5,304,195 | 4/1994 | Twyford, Jr. et al. . |
| 5,312,415 | 5/1994 | Palermo . |
| 5,314,472 | 5/1994 | Fontaine . |
| 5,334,210 | 8/1994 | Gianturco . |
| 5,336,205 | 8/1994 | Zenzen et al. . |
| 5,342,387 | 8/1994 | Summers . |
| 5,350,397 | 9/1994 | Palermo et al. . |
| 5,350,398 | 9/1994 | Pavcnik et al. . |
| 5,354,295 | 10/1994 | Guglielmi et al. . |
| 5,382,259 | 1/1995 | Phelps et al. . |
| 5,383,887 | 1/1995 | Nadal . |
| 5,395,390 | 3/1995 | Simon et al. . |
| 5,405,377 | 4/1995 | Cragg . |
| 5,423,829 | 6/1995 | Pham et al. . |
| 5,423,849 | 6/1995 | Engelson et al. . |
| 5,441,516 | 8/1995 | Wang et al. . |
| 5,443,478 | 8/1995 | Purdy . |
| 5,454,795 | 10/1995 | Samson . |
| 5,514,176 | 5/1996 | Bosley, Jr. . |
| 5,522,836 | 6/1996 | Palermo . |
| 5,527,338 | 6/1996 | Purdy . |
| 5,536,274 | 7/1996 | Neuss . |
| 5,549,624 | 8/1996 | Mirigian et al. ........................ 606/191 |
| 5,562,641 | 10/1996 | Flomenblit et al. . |
| 5,569,245 | 10/1996 | Guglielmi et al. . |
| 5,582,619 | 12/1996 | Ken . |
| 5,601,593 | 2/1997 | Freitag . |
| 5,607,445 | 3/1997 | Summers . |
| 5,624,461 | 4/1997 | Mariant . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,082 | 7/1997 | Sung et al . |
| 5,649,949 | 7/1997 | Wallace et al. . |
| 5,667,522 | 9/1997 | Flomenblit et al. . |
| 5,669,931 | 9/1997 | Kupiecki et al . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,725,552 | 3/1998 | Kotula et al . |
| 5,766,219 | 6/1998 | Horton . |

OTHER PUBLICATIONS

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck and Spine" Sep. 1975; pp. 275–287.

Stephen L. Kaufman, M.D. et al. Investigative Radiology, May–Jun. 1978 "Transcatheter Embolization with Microfibrillar Collagen in Swine"; pp. 200–204.

Ashok J. Kumar, et al. Journal of Neuroradiology (1982) "Preoperative Embolization of Hypervascular Head and Neck Neoplasms using Microfibrillar Collagen", pp. 163–168.

Richard E. Latchaw, M.D. et al., Radiology (1979) "Polyvinly Foam Embolization of Vascular and Neoplastic Lesions of the Head, Neck and Spine" pp. 669–679.

Stewart R. Reuter, M.D. et al. American Journal of Radiology, Sep. 1975 "Selective Arterial Embolization for Control of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

Sidney Wallace, M.D. et al., Cancer, Oct. 1979 "Arterial Occlusion of Pelvic Bone Tumors"; pp. 322–325 & 661–66.

"Mechanical Devices for Arterial Occlusion" By C. Gianturco, M.D. et al., Jul. 1975 pp. 428–435.

"Therapeutic Vascular Occlusion Utilzing Steel Coil Technique: Clinical Applications" By Sidney Wallace, et al., Am J. Roentgenol (1976); pp. 381–387.

"Transcatheter Intravascular Coil Occlusion of Experimental Arteriovenous Fistulas", by James H. Anderson, et al., Am. J. Roentgenol, Nov. 1977, pp. 795–798.

"'Mini' Gianturco Stainless Steel Coils for Transcatheter Vascular Occlusion" by James H. Anderson, et al., From the Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

Standard, et al.; Retrieval of a Guglielmi Detachable Coil After Unraveling and Fracture: Case Report and Experimental Results.; Neurosurgery vol. 35; No. 5 pp. 994 –999; Nov. 1994.

Duckwiler, et al.; Catheters, emblic agents spark neurointervention; Diagnostic Imaging; pp. 66–70, 102; May 1994.

McGraw Hill Encyclopedia of Engineering, Second Edition, Shape Memory Alloys; pp1095 –1096.

ANATOMICALLY SHAPED VASOOCCLUSIVE DEVICE AND METHOD OF MAKING THE SAME

This is a continuation of application Ser. No. 08/799,439 filed Feb. 13, 1997, now U. S. Pat. No. 5,766,219, which is a continuation of Ser. No. 08/425,106 filed Apr. 20, 1995 (now U.S. Pat. No. 5,645,558).

FIELD OF THE INVENTION

This invention relates to the field of vasoocclusive devices. More particularly, it relates to a vasoocclusive device which, as used, is in the approximate shape of an anatomical cavity. The devices may be ultimately deployed through a catheter.

BACKGROUND OF THE INVENTION

Vasoocclusion devices are surgical implants that are placed within the vasculature of the human body, typically via a catheter, either to block the flow of blood through a vessel making up that portion of the vasculature through the formation of an embolus or to form such an embolus within an aneurysm stemming from the vessel. One widely used vasoocclusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vasoocclusive coil that assumes a linear helical configuration when stretched, and assumes a folded, convoluted configuration when relaxed. The stretched configuration is used in placing the coil at the desired site, e.g. by its passage through a catheter. Once the device is so placed, the coil assumes a relaxed configuration, which is better suited to occlude the vessel. Ritchart et al. describes a variety of shapes. The secondary shapes of the disclosed coils include "flower" shapes and double vortices. A random shape is described, as well. These prior vasoocclusive devices do not maintain a three-dimensional conformation for a satisfactory period of time; the coils collapsing in upon themselves to form mere rings. A useful substantially spherical vasoocclusive device has heretofore not been made available.

Vasoocclusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration, and when released from the catheter, form a relaxed and folded shape in the lumen or cavity chosen within the human body. The fibrous elements shown in Chee et al. enhance the ability of the coil to fill the space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vasoocclusive coil assembly having an interlocking ball and keyway-type coupling. U.S. Pat. No. 5,304,195, to Twyford et al., shows a pusher-vasoocclusive coil assembly having an extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vasoocclusive coil.

Vasoocclusive coils having little or no inherent secondary shape have also been described. For instance, in U.S. patent application Ser. No. 07/978,320, filed Nov. 18, 1992, entitled "Ultrasoft Embolization Coils with Fluid-Like Properties" by Berenstein et al., is found a coil having little or no shape after introduction into the vascular space.

Common to all of these devices described above is the characteristic of lacking a spheroid shape when relaxed. Additionally, the concept of a plurality of concentrically nested spherical vasoocclusive devices is lacking in the prior art.

SUMMARY OF THE INVENTION

This invention is a vasoocclusive device comprising one or more strands, or vasoocclusive members, which are wound to form a generally spherical or ovoid shape when relaxed. The strand is made of a flexible material movable between an inoperable substantially linear configuration for insertion into and through a means for delivering the device to a cavity, and an operable, substantially spherical configuration for occluding at least a portion of said cavity.

The vasoocclusive member itself may be a helically wound coil or a co-woven braid typically comprising a biocompatible metal. Fibrous materials may be woven into the member or tied or wrapped onto it. Desirably, in the operable configuration, the device is of a size and shape suitable for fitting snugly within a vascular cavity or vesicle (e.g., an aneurysm, or perhaps, a fistula). The device may be adapted with multiple portions of different substantially spherical sizes, which when relaxed and in the operable configuration nest concentrically, or non-concentrically, with each other within the vascular cavity.

The device may be made in a variety of ways. Typically, the strand is first helically wound or braided in a generally linear fashion. After completion of that step, the strand is then wound around an appropriately shaped mandrel or form and heat-treated in such a fashion that it will retain its shape after removal from the heating form. Auxiliary fibrous materials are then added by weaving, tying, or other suitable permanent attachment methods.

The device is used simply by temporarily straightening the device into the inoperable configuration and introducing it into a suitable catheter, the catheter already having been situated so that its distal opening is within the mouth of the vascular crevice or opening to be filled. The device is then pushed through the catheter and, upon its emanation at the distal end of the catheter into the vascular cavity, assumes its relaxed operable configuration.

DETAILED DESCRIPTION OF THE INVENTION

Figure 1:
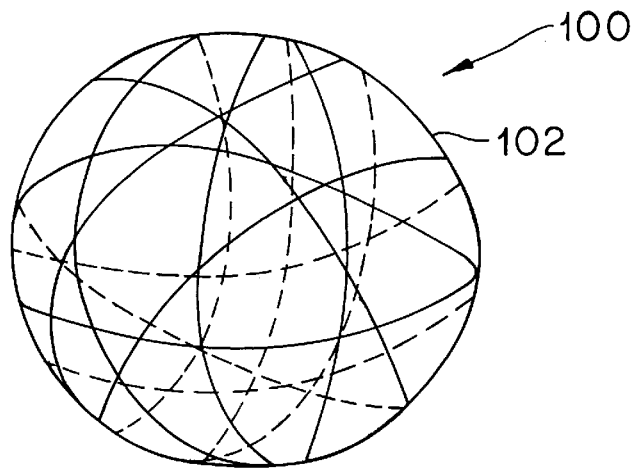
FIG. 1 shows a side view of a spherical device made according to the invention.

FIG. 1 shows one highly desirable embodiment of this invention, a substantially spherical occlusive device (100) in the operable configuration. The occlusive device (100) comprises at least one strand (102) of flexible material movable between an inoperable substantially linear configuration for insertion into and through a means for delivering the device to a desired portion of a vesicle, and an operable, substantially spherical configuration for occluding at least a portion of said vesicle. Preferably, the vesicle is an artery and the desired portion is an aneurysm, however, the invention contemplates that any bodily vesicle or cavity may be occluded by the device. The strand (102) shown is wound in a tertiary substantially spherical structure so as to have multiple loops spaced generally equally to form a cavity, or cage-like structure. The rear side strand (102) loops are shown as dotted lines for clarity, however, these would be visible through the open areas of the cage. It is clearly not necessary that the tertiary shape be precisely a sphere, but it is desirable from a mechanical point of view that such a spacing be approached. The invention contemplates that the occlusive device (100) is wound into and is self-forming into a substantially spherical or distorted spherical form.

In one embodiment, it is intended that the device (100) in the operable configuration be in a roughly spherical cavity or cage-like structure where at least 90–95% of the strand (102) is in the outer 10–15% of the diameter of the device (100). The precise number of loops of the strand will vary and depends upon the type of vesicle or cavity to be filled, and upon the length of catheter tubing necessary for deployment in the extended, linear position.

Figure 2:
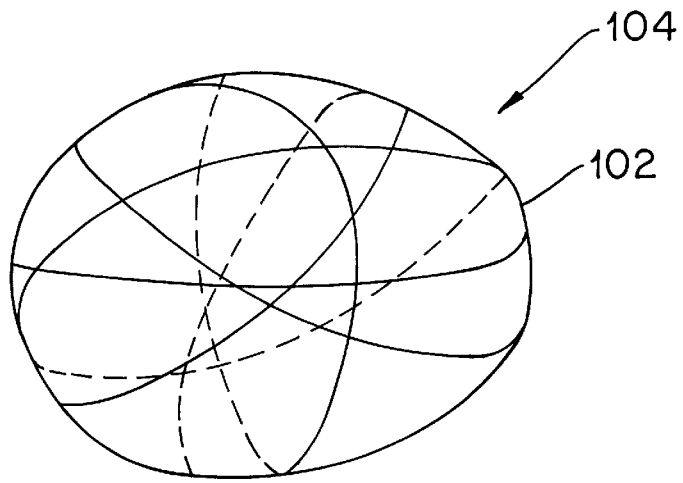
FIG. 2 shows a side view of a device having an oval cross-section made according to the invention.

FIG. 2 shows a variation of the invention in side view in which the shape of the anatomically conforming vasoocclusive device (104) is oval or egg-shaped, yet still substantially spherical in the operable configuration. Other than the final shape of the FIG. 2 device (104), it is similar to that shown in FIG. 1. It is of little importance which axis of the ovoid structure is the major axis and which is the minor axis. In general, it is desirable that the device (104) be constructed in such a way that the resulting relaxed device (104) have a shape similar to the cavity into which it is placed. Somewhat less spherical configurations of the device are permissible and, in many instances, even desired, depending upon the anatomical shape of the vesicle or cavity to be occluded. The substantially spherical shape prevents the vasoocclusive device from collapsing upon itself. By the term "substantially spherical" is meant a shape which includes spherical as well as other distorted shapes, such as ovate, ovoid, or ellipsoid, but in any event having two orthogonal cross sections which are closed shapes having no substantially straight sides.

The material used in the occlusive device (100) may be any of a wide variety of materials. Preferably, the strand (102) is a wire constructed of a radiopaque material such as a metal or a polymer. Suitable metals and alloys for the wiring include Platinum Group metals, especially platinum rhodium palladium, as well as tungsten, gold, silver, tantalum, and alloys of these metals. Highly preferred is a platinum/tungsten alloy.

The wire may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel, and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as nitinol. These are very sturdy alloys which will tolerate significant flexing without deformation even when used as a very small diameter wire. Additionally, the strand may be constructed of a polymer, such as polyvinyl alcohol foam, for example.

Generally speaking, when the device (100) is formed of a metal such as platinum or a super-elastic alloy such as nitinol, the diameter of the wire used in the production of the coil will be in the range of 0.0005 and 0.006 inches. The wire of such diameter is typically then wound into a coil having a primary diameter of between 0.005 and 0.018 inches. The preferable diameter is 0.010 to 0.018 inches. The wire should be of sufficient diameter to provide a hoop strength to the resulting device sufficient to hold the device (100) in place within the chosen body cavity without distending the wall of the cavity and without moving from the cavity as a result of the repetitive fluid pulsing found in the vascular system. Obviously, should a super-elastic alloy such nitinol be used, the diameter of the coil wire can be significantly smaller than that used when the relatively ductile platinum or platinum/tungsten alloy is used as the material of construction. Finally, as regards FIG. 1, the overall diameter of the device (100) in the operable configuration is generally between 3 and 40 millimeters. Most aneurysms within the cranial vasculature can be treated by one or more devices having those diameters.

Figure 3:
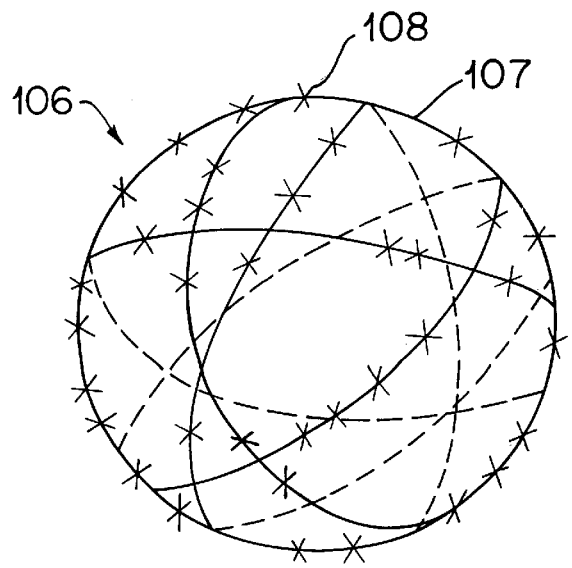
FIG. 3 shows a side view of a device made according to the invention using a thrombogenic fiber.

As can be seen in FIG. 3, the occlusive strand (107) may be adapted with fibers (108) such as synthetic radiolucent fibers or polymers (or metallic threads coated with radiolucent or radiopaque fibers) such as dacron (polyester), polyglycolic acid, polylactic acid, fluoropolymers (polytetrafluoro-ethylene), nylon (polyamide), or even silk. Natural fibers such as silk, cotton or wool may also be employed. Should a fiber be used as the major component of the strand (102), it is desirably filled with some amount of a known radiopaque material such as powdered tantalum powdered tungsten bismuth oxide, barium sulfate, and the like.

The fibrous elements incorporated into the braid may be a bundle of individual fibers, e.g., between 5 and 100 fibers per fibrous bundle, preferably 20–30 fibers per bundle, or may be monofilaments. As was noted above, it may be desirable in certain circumstances to add fibrous materials outlying the vasoocclusive core so to provide additional bulk and area for creation of thrombosis.

Figure 4:
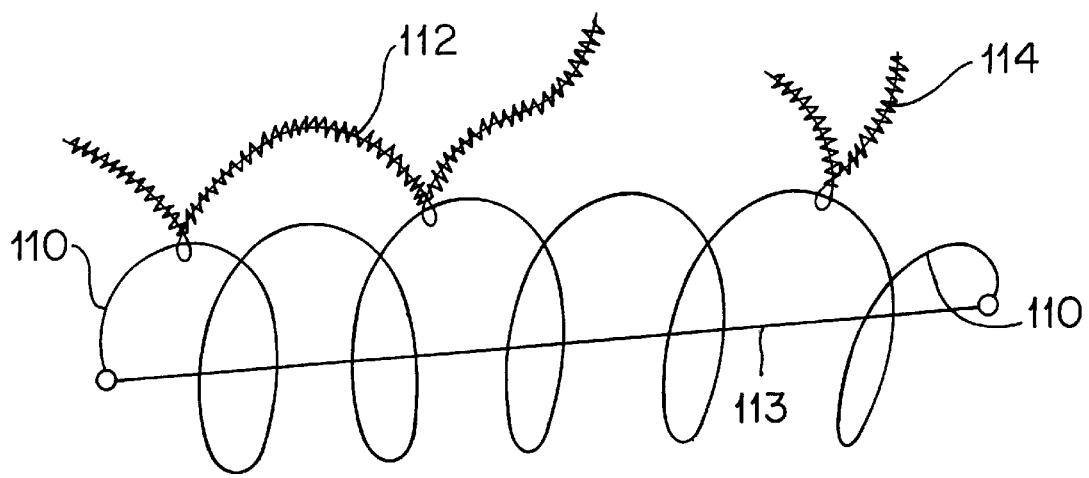
FIG. 4 shows a magnified section of a helical coil as could be used in the inventive device having filamentary material attached through the loop of the device.

FIG. 4 shows a magnified side view of a portion of a helically coiled vasoocclusive strand (110) as may be used in the variations of the invention. Shown attached to the coiled vasoocclusive strand (110) are fibrous polymeric materials (112, 114) attached to the member (110) by distinct two methods. First is a series of looping fibers (112), which are looped through or tied to the strand (110) and continue axially down the coil. Another variation is the tuft (114) shown tied or otherwise affixed to the strand (110). Tufts (114) are tied at multiple sites through the coiled strand (110) so to provide a vast area of thrombus forming sites.

The occlusive strand (110) in FIG. 4 is shown to have a secondary structure of helically wound flexible material. The helixes provide further support to the substantially spherical form when in the operable configuration. In another variation of the invention in which the device can comprise a plurality of small, braided strands (not shown). The strands can be braided elements made partially of regularly or randomly included radiopaque wires. Again, the braid may optionally be partially woven of, or co-woven with, fibers. The wire or fibers used in the production of the braid will typically be fairly small, e.g., in the range of 0.0005 to 0.0015 inches. The resulting woven braid diameter will normally be 0.008 to 0.018 inches. The braided structure is typically not as compliant as is that of a coiled secondary structure. Consequently, a more ductile material such as platinum may be preferable in such a device. The braid structure permits introduction of natural or synthetic fibrous materials such as Dacron and the other filaments noted below which promote formation of a thrombus.

Additionally, the invention contemplates that a safety wire (not shown) may be inserted through the longitudinal axis of the helically coiled strand to provide structural support. Alternatively, the safety wire may be first formed to be flexibly disposed in a substantially spherical form, and then inserted through the longitudinal axis of a helically coiled strand which has not been preformed in a substantially spherical form.

Figure 5:
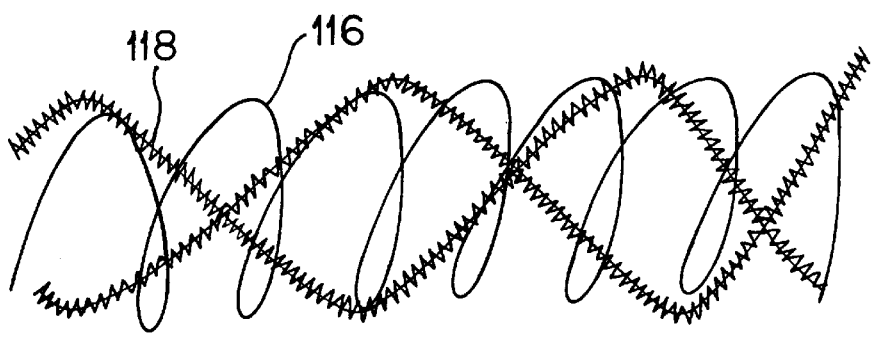
FIG. 5 shows a magnified section of a helical coil covered by an outer fibrous braided covering.
Figure 6D:
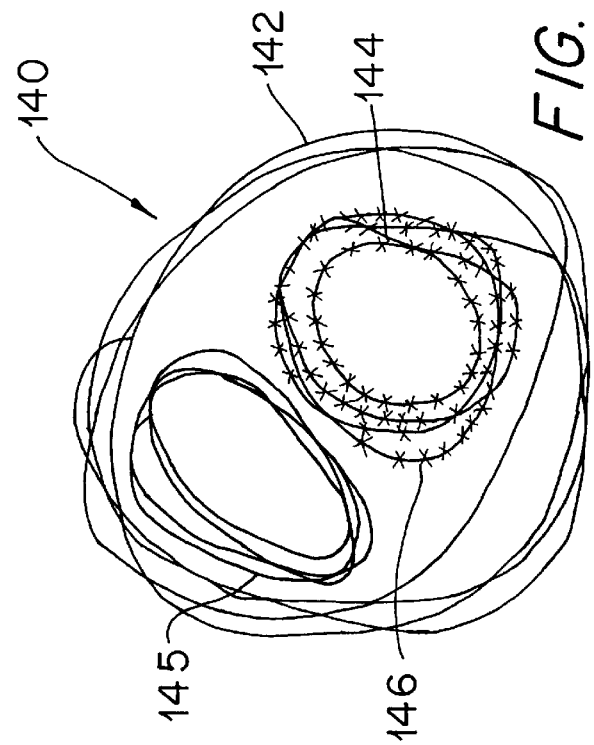
FIG. 6A shows a central cross-section of an alternative embodiment having a vasoocclusive sphere covered with fibers positioned within a first vasoocclusive sphere as it would appear when deployed within a portion of a vesicle.
FIG. 6B shows a side view of the alternative embodiment shown in FIG. 6 in the wound configuration, but not deployed in a vesicle.
Figure 6C:
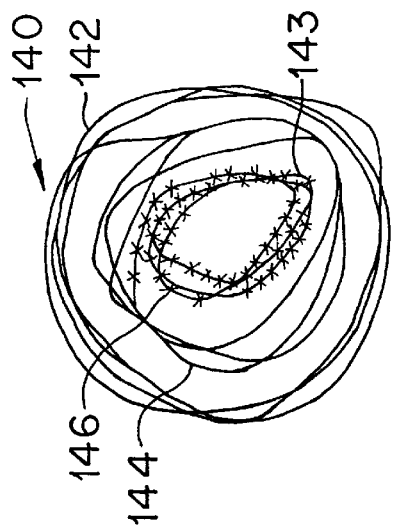
Figure 6B:
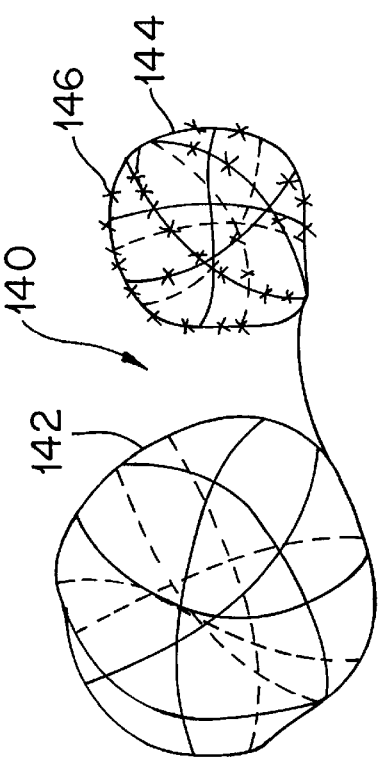

FIG. 5 shows still another variation and method for increasing the thrombogenic capability and rate of the device. FIG. 7 shows an embolic, helically shaped strand (116) co-woven with and covered by a fibrous braid (118). One method for producing the variation shown in FIG. 6 is described in U.S. Pat. Nos. 5,226,911 and 5,304,194 to Chee. One manner of producing the variation shown in FIG. 7 is described in U.S. patent application Ser. No. 07/965, 973, filed Oct. 26, 1992, to Phelps and Vann. One manner of making a co-woven braid using radiopaque fibers is shown in U.S. patent application Ser. No. 08/005,478, filed Jan. 15, 1993, to Engelson and Samson. Each of these techniques may be used in making the vasoocclusive devices described herein however, other similar techniques will be known to the skilled artisan.

It is within the scope of this invention that procedures for incorporating first substantially spherical occlusive devices of this invention into an aneurysm or other vascular vesicle can be followed by introduction of other occlusive devices into the center of the cavity formed by the first occlusive device to produce superior physical stability.

Figure 6A:
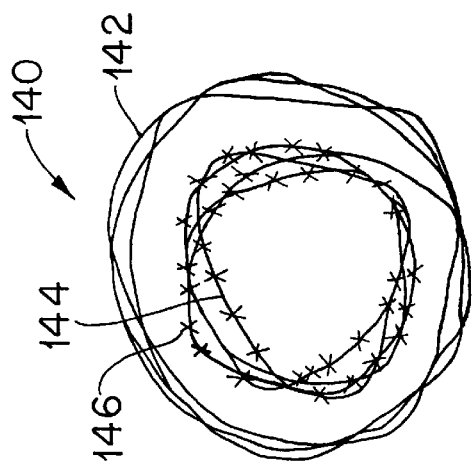
Figure 7:
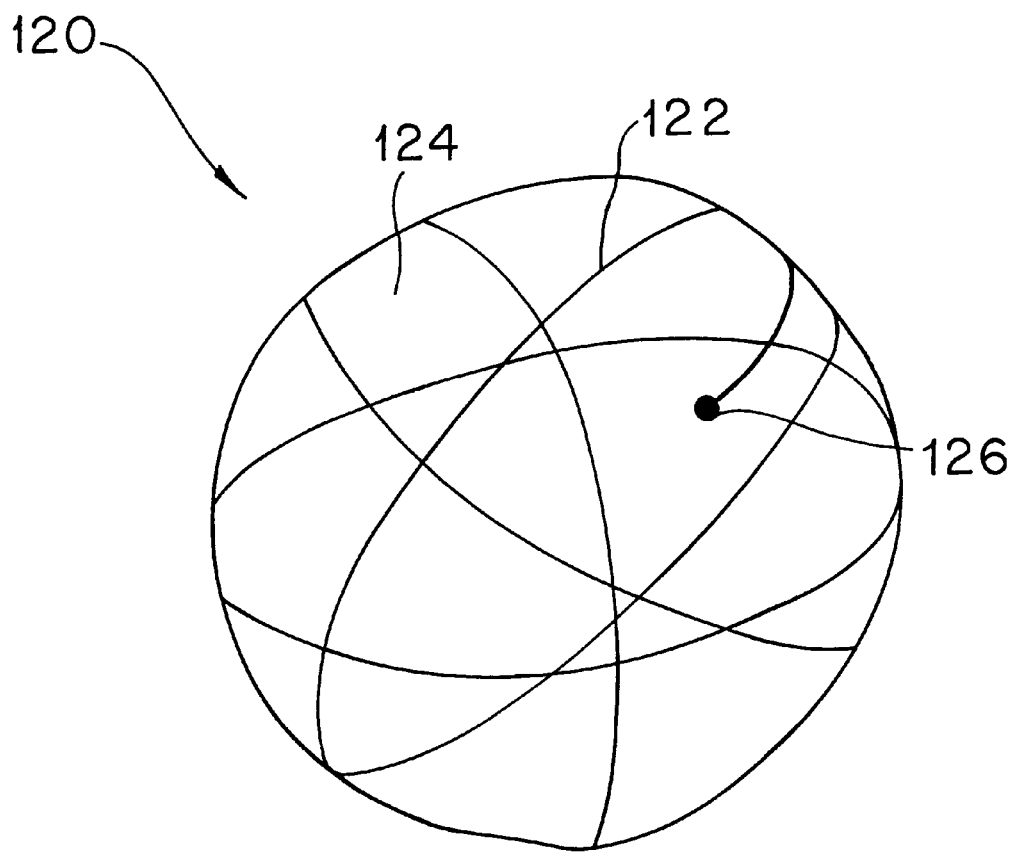
FIG. 7 shows a mandrel suitable for winding making a device according to the invention.

FIG. 6A shows a cross-section of such an alternative embodiment of the invention, wherein two vasoocclusive strand portions (142, 144) are provided to nest concentrically with each other in the operable configuration. The larger vasoocclusive strand portion (142) can serve as a cavity in which to concentrically house the other smaller vasoocclusive strand portion (144). When the device (140) is unwound in the inoperable configuration, each vasoocclusive strand portion (142, 144) is aligned longitudinally in tandem. Such a vasoocclusive device (140) with a plurality of concentric vasoocclusive portions can be made from the same metallic strand along different portions thereof, or separate strands can be prepared and then fused together at their ends in longitudinal tandem. FIG. 6B shows this alternative embodiment in a partially unwound position to demonstrate that the spheres are arranged in tandem along the same strand. The aligned vasoocclusive strand portions (142, 144) can each be wound on the same or slightly different sized mandrel in order to form a multiple-layered sphere when positioned in the wound, operable configuration.

The invention contemplates that a plurality of concentrically nesting occlusive strand portions may be employed. Each spherical occlusive strand portion may have a unique size, so that the device is capable of concentric nesting with the other occlusive members. The invention also contemplates that a plurality of substantially spherical strand portions, or other known vasoocclusive devices, can be inserted in a non-concentric manner inside a substantially spherical cavity created by the first strand portion. To protect flowing blood from a thrombogenic surface, the outermost coils may be bare, or unfibered. Providing natural or synthetic fibers (146) to the innermost strand portion (144) increases the thrombogenicity therein and protects the vesicle from flowing blood. In this way, blood clotting begins in the center of the vasoocclusive device and proceeds outward, stopping at the arterial lumen.

FIG. 7 depicts a mandrel (120) suitable for making a substantially spherical vasoocclusive device. As shown, the mandrel (120) can primarily consist of a core (124). The core (124) is typically made of a refractory material, such as alumina or zirconia. The function of the core (124) is simply to form a support for winding that will not pollute the vasoocclusive device during the heat-treatment step to be described below, and will provide a specific substantially spherical form for the vasoocclusive device during the heat-treatment step. Circumferentially continuous grooves (122) on the surface of the core (124) may be preferably provided to assist in regularly aligning the strand as it is being wound about the core (124). Additionally, a small strand receptacle (126) may be provided to insert and hold the end or ends of the strand in place when performing the heating step. Other methods of winding a strand around a core will be apparent to one skilled in the art. The continuous grooves (122) are preferably provided to permit the strand to be wound about the core (124) with minimal kinking or angulation of the coils.

If the entire then-wound vasoocclusive device is metallic, it may be placed in an oven at an appropriate temperature to "set" or impart the substantially spherical form to the device. If the device is a platinum alloy or of nitinol, such a temperature is 1100 degrees Fahrenheit, for 4 hours to provide a modest amount of preshaping to the resulting vasoocclusive device. Should the make-up of the vasoocclusive device not be solely metal, in that it contains readily meltable plastic or the like, the temperature at which the heat treatment takes place is significantly lower and typically for a significantly shorter period of time. The flexural modulus of most plastics being significantly lower than that of metals, the bulk of the polymer-based device will be significantly larger than that of the metal-based device.

After cooling, the device is removed from the core (124). Any filamentary fibrous material may then attached to the strand as described above. The vasoocclusive device is then placed in a cannula or catheter for delivery in the inoperable substantially linear configuration into a selected body cavity or vesicle, where it then assumes the operable substantially spherical configuration.

Practitioners in this medical device area will undoubtedly have other ways of producing the noted anatomically shaped occlusive and vasoocclusive devices. The vasoocclusive devices of this invention may be used in a manner similar to those methods described in U.S. Pat. No. 4,994,069. Briefly, the inventive devices are typically to supplied in a prepackaged form in a sterile cannula which is adapted to engage the proximal end of a catheter. Once the catheter is in place within a vessel and the distal end of the catheter is placed into, e.g., a mouth of an aneurysm, the vasoocclusive device is inserted into the aneurysm, where it assumes its relaxed shape. Although the device may be used with a flexible pusher without connection to the vasoocclusive device described here, much more desirable is the use of a mechanically detachable coupling on the vasoocclusive device and the pusher. Any of the mechanically detachable couplings described above in the Background of the Invention would be suitable in this instance.

Throughout this application various publications are referenced. The disclosures of these publications in their entireties are hereby incorporated by reference into this application in order to more fully describe the state of the art to which the invention pertains.

The examples herein are intended to illustrate, but not limit, the present invention. While they are typical of those that might be used, other procedures known to those skilled in the art may alternatively be employed.

EXAMPLE

Transparent, elastic, vesicle models were constructed with two rows of lateral wall aneurysms for comparison: two each at diameters of 10, 8, 6, and 4 millimeters. One row had narrow necks (less than 50% of aneurysm diameter), the other had wide necks (greater than 50% of aneurysm diameter). The models were perfused with both Newtonian and with non-Newtonian fluids flowing at physiologic volumes and pulse profiles. Isobaric dyes were injected and the flow dynamics observed. Various sizes and kinds of previously known coils, such as the Guglielmi Detachable Coil were, delivered to the aneurysms, in addition to various sizes of the devices of the present invention, and the changes in flow dynamics were observed and compared.

The angular velocities within the aneurysm were observed to vary inversely with aneurysm diameter. That is to say that smaller aneurysms had a faster angular flow velocities, however, both small-neck aneurysms and wide-neck aneurysms were observed to have high angular flow velocities. Aneurysms with wider necks were observed to have more rapid peripheral flow than those with smaller necks.

The spherical vasoocclusive devices of the present invention introduced into the aneurysms markedly decreased the angular and peripheral velocity by creating more internal friction and/or by better insulating the fluid in the aneurysm from that section of the parent artery. Such an improved stasis of blood flow is critical to the success of the invention to promote blood clot formation. As compared to other available coils tested, the vasoocclusive devices of the present invention were very surprisingly successful and yielded unexpectedly improved results.

The vasoocclusive devices remained stable and in a substantially spherical form within the aneurysms, especially that made from 0.004-inch platinum wire and inserted into the smaller aneurysms. This was in contrast to the other available coil devices tested, which had a tendency to collapse into ring forms when disturbed, as by the introducing catheter tip. In larger aneurysms, especially those with wide necks, the greater hoop strength of the vasoocclusive devices of the present invention provided the desirable physical stability within the aneurysm.

What is claimed is:

1. A method of making an occlusive device comprising a strand of a flexible material movable between an inoperable substantially linear configuration for insertion into and through a means for delivering the device to a desired portion of a vesicle, and an operable, substantially spherical configuration for occluding at least a portion of said vesicle, the method comprising the steps of:

winding a strand of flexible material including a radiopaque material onto a core having a substantially spherical form;

heating the core and the strand to impart a substantially spherical form to said strand; and removing said strand from said core, thereby producing said occlusive device.

2. The method of claim 1, wherein said step of heating comprises heating the core and the strand to approximately 1100° F.

3. The method of claim 1, further comprising the step of connecting at least one fiber connected to said strand.

* * * * *

UNITED STATES PATENT AND TRADEMARK OFFICE
CERTIFICATE OF CORRECTION

PATENT NO. : 6,090,125
DATED : Jul. 18, 2000
INVENTOR(S) : Joseph A. Horton

It is certified that error appears in the above-identified patent and that said Letters Patent is hereby corrected as shown below:

Title page, under "U.S. PATENT", change "4,097,336" to read --4,907,336--.

Column 3, line 25, after "vesicle. add the following two paragraphs:

--FIG. 6C shows an alternative embodiment having a vasoocclusive spherical portion incorporating fibers positioned within a first vasoocclusive sphere and a second vasoocclusive sphere, in nested configuration.

FIG. 6D shows both a vasoocclusive spherical portion incorporating fibers and a vasoocclusive spherical portion not incorporating fibers separately contained within a first spherical vasoocclusive sphere.--.

UNITED STATES PATENT AND TRADEMARK OFFICE
CERTIFICATE OF CORRECTION

PATENT NO. : 6,090,125
DATED : Jul. 18, 2000
INVENTOR(S) : Joseph A. Horton

It is certified that error appears in the above-identified patent and that said Letters Patent is hereby corrected as shown below:

Column 6, line 25, after "tion.", add the following paragraph:

-- The invention, as shown in FIG. 6C, contemplates that a plurality of concentrically nesting occlusive strand portions (143) may be employed. Each spherical occlusive strand portion may have a unique size, so that the device is capable of concentric nesting with the other occlusive members. The invention, as shown in FIG. 6D, also contemplates that a plurality of substantially spherical strand portions (145), or other known vasoocclusive devices, can be inserted in a nonconcentric manner inside a substantially spherical cavity created by the first strand portion. To protect flowing blood from a thrombogenic surface, the outermost coils may be bare, or unfibered. Providing natural or synthetic fibers (146) to the innermost strand portion (144) increases the thrombogenicity therein and protects the vesicle from flowing blood. In this way, blood clotting begins in the center of the vasoocclusive device and proceeds outward, stopping at the arterial lumen. -- .

Signed and Sealed this

Twenty-fourth Day of April, 2001

Attest:

NICHOLAS P. GODICI

Attesting Officer

Acting Director of the United States Patent and Trademark Office